US009789228B2

(12) United States Patent
Tramontano et al.

(10) Patent No.: US 9,789,228 B2
(45) Date of Patent: Oct. 17, 2017

(54) ANTIMICROBIAL COATINGS FOR MEDICAL DEVICES AND PROCESSES FOR PREPARING SUCH COATINGS

(71) Applicant: Covidien LP, Mansfield, MA (US)

(72) Inventors: Valentino J. Tramontano, Brockton, MA (US); Brent Marsden, Reading, MA (US); Robert F. Almeida, Norton, MA (US); Eric W. Dahl, Ann Arbor, MI (US); James W. Rawlins, Hattiesburg, MS (US); Sharathkumar K. Mendon, Hattiesburg, MS (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/567,183

(22) Filed: Dec. 11, 2014

(65) Prior Publication Data
US 2016/0166738 A1    Jun. 16, 2016

(51) Int. Cl.
| | | |
|---|---|---|
| A61L 29/08 | (2006.01) | |
| A61L 29/16 | (2006.01) | |
| A61L 27/34 | (2006.01) | |
| A61L 27/54 | (2006.01) | |
| A61L 31/10 | (2006.01) | |
| A61L 31/16 | (2006.01) | |
| A61L 17/14 | (2006.01) | |

(52) U.S. Cl.
CPC .......... *A61L 29/085* (2013.01); *A61L 17/145* (2013.01); *A61L 27/34* (2013.01); *A61L 27/54* (2013.01); *A61L 29/16* (2013.01); *A61L 31/10* (2013.01); *A61L 31/16* (2013.01); *A61L 2300/104* (2013.01); *A61L 2300/206* (2013.01); *A61L 2300/224* (2013.01); *A61L 2300/404* (2013.01); *A61L 2300/45* (2013.01); *A61L 2300/602* (2013.01); *A61L 2420/02* (2013.01); *A61L 2420/06* (2013.01)

(58) Field of Classification Search
CPC ........ A61L 27/34; A61L 27/54; A61L 29/085; A61L 29/16; A61L 31/10; A61L 31/16; A61L 17/145; A61L 2300/224; A61L 2420/06; A61L 2300/602; A61L 2300/104; A61L 2300/206; A61L 2420/02; A61L 2300/45; A61L 2300/404
See application file for complete search history.

(56) References Cited

U.S. PATENT DOCUMENTS

| | | | |
|---|---|---|---|
| 3,932,627 A | 1/1976 | Margraf | |
| 4,656,083 A | 4/1987 | Hoffman et al. | |
| 4,994,071 A | 2/1991 | MacGregor | |
| 5,013,306 A | 5/1991 | Solomon et al. | |
| 5,019,096 A * | 5/1991 | Fox, Jr. ................. | A01N 25/24 2/167 |
| 5,217,492 A | 6/1993 | Guire et al. | |
| 5,246,451 A | 9/1993 | Trescony et al. | |
| 5,295,979 A | 3/1994 | DeLaurentis et al. | |
| 5,360,440 A | 11/1994 | Andersen | |
| 5,409,696 A | 4/1995 | Narayanan et al. | |
| 5,419,760 A | 5/1995 | Narciso, Jr. | |
| 5,449,382 A | 9/1995 | Dayton | |
| 5,455,040 A | 10/1995 | Marchant | |
| 5,464,650 A | 11/1995 | Berg et al. | |
| 5,496,276 A | 3/1996 | Wang et al. | |
| 5,498,248 A | 3/1996 | Milder | |
| 5,534,287 A | 7/1996 | Lukic | |
| 5,567,495 A | 10/1996 | Modak et al. | |
| 5,591,140 A | 1/1997 | Narayanan et al. | |
| 5,591,225 A | 1/1997 | Okuda | |
| 5,609,629 A | 3/1997 | Fearnot et al. | |
| 5,616,338 A | 4/1997 | Fox, Jr. et al. | |
| 5,618,316 A | 4/1997 | Hoffman et al. | |
| 5,624,411 A | 4/1997 | Tuch | |
| 5,624,449 A | 4/1997 | Pham et al. | |
| 5,634,941 A | 6/1997 | Winston et al. | |
| 5,643,580 A | 7/1997 | Subramaniam | |
| 5,653,747 A | 8/1997 | Dereume | |
| 5,665,103 A | 9/1997 | Lafontaine et al. | |
| 5,667,523 A | 9/1997 | Bynon et al. | |
| 5,674,241 A | 10/1997 | Bley et al. | |
| 5,693,085 A | 12/1997 | Buirge et al. | |
| 5,697,971 A | 12/1997 | Fischell et al. | |

(Continued)

FOREIGN PATENT DOCUMENTS

| | | |
|---|---|---|
| DE | 19535068 A1 | 3/1997 |
| EP | 1000591 A2 | 5/2000 |
| JP | 2008-173461 A | 7/2008 |
| JP | 2009-502420 A | 1/2009 |
| JP | 2009-240490 A | 10/2009 |

(Continued)

OTHER PUBLICATIONS

Bilgili et al., "Nano-milling of pigment agglomerates using a wet stirred media mill: Elucidation of the kinetics and breakage mechanisms", Chem. Eng. Sci. 2006(61(1)), pp. 149-157.
U.S. Appl. No. 14/317,587, filed Jun. 27, 2014.
Zhang, et al., "Superlow Fouling Sulfobetaine and Carboxybetaine Polymers on Glass Slides," Langmuir, 2006, vol. 22, pp. 10072-10077.
Luzinov, et al.,, "Epoxy-Terminated Self-Assembled Monolayers: Molecular Glues for Polymer Layers," Langmuir, 2000, vol. 16, pp. 504-516.

(Continued)

*Primary Examiner* — Brian-Yong Kwon
*Assistant Examiner* — Doan Phan
(74) *Attorney, Agent, or Firm* — Kenneth Collier; Jessica Kwak Rauckman

(57) ABSTRACT

Antimicrobial formulations and coatings for medical devices and processes therefor are disclosed. The formulations include at least one water permeable polymer with at least one antimicrobial agent in a liquid medium and are prepared by wet milling the components and can form antimicrobial coatings having uniformly dispersed particles having an average size of no greater than 50 microns.

15 Claims, 9 Drawing Sheets

(56) References Cited

U.S. PATENT DOCUMENTS

| | | |
|---|---|---|
| 5,741,327 A | 4/1998 | Frantzen |
| 5,770,255 A | 6/1998 | Burrell et al. |
| 5,776,141 A | 7/1998 | Klein et al. |
| 5,824,045 A | 10/1998 | Alt |
| 5,824,049 A | 10/1998 | Ragheb et al. |
| 5,824,077 A | 10/1998 | Mayer |
| 5,837,313 A | 11/1998 | Ding et al. |
| 5,843,117 A | 12/1998 | Alt et al. |
| 5,866,113 A | 2/1999 | Hendriks et al. |
| 5,873,904 A | 2/1999 | Ragheb et al. |
| 5,888,577 A | 3/1999 | Griffin, III et al. |
| 5,897,911 A | 4/1999 | Loeffler |
| 5,902,283 A | 5/1999 | Darouiche et al. |
| 5,911,754 A | 6/1999 | Kanesaka et al. |
| 5,948,018 A | 9/1999 | Dereume et al. |
| 5,957,974 A | 9/1999 | Thompson et al. |
| 5,968,069 A | 10/1999 | Dusbabek et al. |
| 5,976,169 A | 11/1999 | Imran |
| 6,010,530 A | 1/2000 | Goicoechea |
| 6,019,789 A | 2/2000 | Dinh et al. |
| 6,022,374 A | 2/2000 | Imran |
| 6,033,719 A | 3/2000 | Keogh |
| 6,051,020 A | 4/2000 | Goicoechea et al. |
| 6,066,167 A | 5/2000 | Lau et al. |
| 6,068,634 A | 5/2000 | Lorentzen Cornelius et al. |
| 6,068,656 A | 5/2000 | Von Oepen |
| 6,106,548 A | 8/2000 | Roubin et al. |
| 6,156,373 A | 12/2000 | Zhong et al. |
| 6,159,531 A | 12/2000 | Dang et al. |
| 6,231,598 B1 | 5/2001 | Berry et al. |
| 6,268,348 B1 | 7/2001 | Bhatnagar |
| 6,306,165 B1 | 10/2001 | Patnaik et al. |
| 6,322,847 B1 | 11/2001 | Zhong et al. |
| 6,371,980 B1 | 4/2002 | Rudakov et al. |
| 6,663,660 B2 | 12/2003 | Dusbabek et al. |
| 6,706,024 B2 | 3/2004 | Modak et al. |
| 6,979,348 B2 | 12/2005 | Sundar |
| 7,077,860 B2 | 7/2006 | Yan et al. |
| 7,198,675 B2 | 4/2007 | Fox et al. |
| 7,258,891 B2 | 8/2007 | Pacetti et al. |
| 7,297,159 B2 | 11/2007 | Hossainy et al. |
| RE40,722 E | 6/2009 | Chappa |
| 7,553,377 B1 | 6/2009 | Chen et al. |
| 7,563,277 B2 | 7/2009 | Case et al. |
| 7,563,324 B1 | 7/2009 | Chen et al. |
| 7,572,336 B2 | 8/2009 | Van Sciver et al. |
| 7,588,642 B1 | 9/2009 | Morris et al. |
| 7,604,700 B2 | 10/2009 | Fox et al. |
| 7,622,070 B2 | 11/2009 | Atladottir et al. |
| 7,632,307 B2 | 12/2009 | Pacetti et al. |
| 7,648,725 B2 | 1/2010 | Van Sciver et al. |
| 7,669,548 B2 | 3/2010 | Chappa |
| 7,704,544 B2 | 4/2010 | Pacetti et al. |
| 7,735,449 B1 | 6/2010 | Harold et al. |
| 7,771,743 B1 | 8/2010 | Luthra et al. |
| 7,820,284 B2 | 10/2010 | Terry |
| 7,823,533 B2 | 11/2010 | Chen et al. |
| 7,939,095 B2 | 5/2011 | Zhao |
| 7,958,840 B2 | 6/2011 | Chappa |
| 7,959,942 B2 | 6/2011 | Cottone |
| 7,985,440 B2 | 7/2011 | Pacetti et al. |
| 7,985,441 B1 | 7/2011 | Tang et al. |
| 8,003,156 B2 | 8/2011 | Van Sciver |
| 8,069,814 B2 | 12/2011 | Guerriero et al. |
| 8,097,291 B2 | 1/2012 | Fredrickson et al. |
| 8,197,879 B2 | 6/2012 | Fox et al. |
| 8,308,699 B2 | 11/2012 | Zhang et al. |
| 8,506,619 B2 | 8/2013 | Ortiz et al. |
| 8,668,919 B2 | 3/2014 | Ludwig et al. |
| 2002/0062145 A1 | 5/2002 | Rudakov et al. |
| 2005/0015142 A1 | 1/2005 | Austin et al. |
| 2005/0107869 A1 | 5/2005 | Sirhan et al. |
| 2005/0137680 A1 | 6/2005 | Ortiz et al. |
| 2005/0158449 A1 | 7/2005 | Chappa |
| 2006/0088653 A1 | 4/2006 | Chappa |
| 2006/0177476 A1 | 8/2006 | Saffran |
| 2007/0003753 A1 | 1/2007 | Asgari |
| 2007/0043428 A1 | 2/2007 | Jennings et al. |
| 2007/0168019 A1 | 7/2007 | Amplatz et al. |
| 2008/0033522 A1* | 2/2008 | Grewe ............... A61L 31/082 623/1.11 |
| 2008/0188830 A1 | 8/2008 | Rosenblatt et al. |
| 2009/0011117 A1 | 1/2009 | Nunez et al. |
| 2009/0029961 A1* | 1/2009 | Modak ............... A01N 47/44 514/184 |
| 2009/0062899 A1 | 3/2009 | Dang et al. |
| 2009/0155335 A1 | 6/2009 | O'Shaughnessey et al. |
| 2009/0254174 A1 | 10/2009 | Case et al. |
| 2010/0152834 A1 | 6/2010 | Hannes et al. |
| 2010/0179644 A1 | 7/2010 | Jennings et al. |
| 2010/0189808 A1 | 7/2010 | Gupta et al. |
| 2010/0191219 A1 | 7/2010 | Gupta et al. |
| 2010/0196434 A1 | 8/2010 | Gupta et al. |
| 2010/0198334 A1 | 8/2010 | Yodfat et al. |
| 2010/0215711 A1 | 8/2010 | Gupta et al. |
| 2010/0233288 A1 | 9/2010 | Gupta et al. |
| 2010/0234815 A1 | 9/2010 | Do et al. |
| 2010/0280587 A1 | 11/2010 | Ortiz et al. |
| 2011/0027368 A1* | 2/2011 | Burgermeister ..... A61K 31/196 424/486 |
| 2011/0027757 A1 | 2/2011 | Kyomoto et al. |
| 2011/0039013 A1 | 2/2011 | Papp et al. |
| 2011/0054589 A1 | 3/2011 | Bashiri et al. |
| 2011/0152998 A1 | 6/2011 | Berez et al. |
| 2011/0208294 A1 | 8/2011 | Cottone |
| 2012/0021038 A1 | 1/2012 | Kloke et al. |
| 2012/0197413 A1 | 8/2012 | Kyomoto et al. |
| 2012/0271396 A1 | 10/2012 | Zheng et al. |
| 2012/0283765 A1 | 11/2012 | Berez et al. |
| 2012/0301528 A1 | 11/2012 | Uhlmann et al. |
| 2012/0301530 A1* | 11/2012 | Uhlmann ............... A01N 59/16 424/405 |
| 2013/0315972 A1* | 11/2013 | Krasnow ............... A01N 25/12 424/409 |
| 2014/0277400 A1 | 9/2014 | Wainwright |

FOREIGN PATENT DOCUMENTS

| | | |
|---|---|---|
| JP | 2012-527912 A | 11/2012 |
| WO | WO-91/02537 A1 | 3/1991 |
| WO | WO-98/10806 A1 | 3/1998 |
| WO | WO-99/37242 A1 | 7/1999 |
| WO | WO-00/61034 A1 | 10/2000 |
| WO | WO-03/017852 A1 | 3/2003 |
| WO | WO-2007/018980 A2 | 2/2007 |
| WO | WO-2008/118132 A1 | 10/2008 |
| WO | WO-2010/136075 A1 | 12/2010 |
| WO | WO-2013/030819 A1 | 3/2013 |
| WO | WO-2014/152608 A1 | 9/2014 |

OTHER PUBLICATIONS

Tsukruk, et al., "Sticky Molecular Surfaces: Epoxysilane Self-Assembled Monolayers," Langmuir, 1999, vol. 15, pp. 3029-3032.

Ehlers, et al., "Theoretical Study on Mechanisms of the Epoxy-Amine Curing Reaction," Macromolecules, 2007, vol. 40, pp. 4370-4377.

Feng, et al., "Atom-Transfer Radical Grafting Polymerization of 2-Methacryloyloxyethyl Phosphorylcholine from Silicon Wafer Surfaces," Journal of Polymer Science: Part A: Polymer Chemistry, 2004, vol. 42, pp. 2931-2942.

Sanchis, et al., "Surface Modification of a Polyurethane Film by Low Pressure Glow Discharge Oxygen Plasma Treatment," Journal of Applied Polymer Science, 2007, vol. 105, pp. 1077-1085.

Sidouni, et al., "Surface Properties of a Specifically Modified High-Grade Medical Polyurethane," Surface Science, 2001, vol. 491, pp. 355-369.

Lin, et al., "Surface Characterization and Platelet Adhesion Studies on Polyurethane Surface Immobilized with C60," Biomaterials, 1999, vol. 20, pp. 1613-1620.

Dow Corning, "A Guide to Silane Solutions," Dow Corning, 2005.

(56) References Cited

OTHER PUBLICATIONS

Chen, et al., "Surfaces Having Dual Fibrinolytic and Protein Resistant Properties by Immobilization of Lysine on Polyurethane Through a PEG Spacer," J Biomed Mater Res, 2009, vol. 90A, pp. 940-946.

Ren, et al., "Hemocompatibility Evaluation of Polyurethane Film with Surface-Grafted Poly(ethylene glycol) and Carboxymethyl-Chitosan," J. Appl Polym Sci, 2013, pp. 308-315.

Yakai, et al., "Surface Modification of Polycarbonate Urethane by Covalent Linkage of Heparin with a PEG Spacer," Trans. Tianjin Univ, 2013, vol. 19, pp. 58-65.

Lee et al., "Covalent Incorporation of Starch Derivative into Waterborne Polyurethane for Biodegradability," Carbohydrate Polymers, 2012, vol. 87, pp. 1803-1809.

Kang, et al., "Fabrication of Biofunctional Stents with Endothelial Progenitor Cell Specificity for Vascular Re-endothelialization," Colloids and Surfaces B: Biointerfaces, 2013, vol. 102, pp. 744-751.

Lewis, et al., "Poly(2-methacryloyloxyethyl phosphorylcholine) for Protein Conjugation," Bioconjugate Chem, 2008, vol. 19, pp. 2144-2155.

Gelest, Inc., "Silane Coupling Agents: Connecting Across Boundaries," version 2.0, 2006.

Love, et al., "Self-Assembled Monolayers of Thiolates on Metals as a Form of Nanotechnology," Chem Rev 2005, vol. 105, pp. 1103-1169.

Bridges, et al., "Advances in Drug Eluting Stents—Focus on the Endeavor® Zotarolimus Stent," Medical Devices: Evidence and Research, 2009, pp. 1-8.

"BiodivYsio™ PMA P000011 Summary of Safety and Effectiveness Data," Biocompatibles Cardiovascular Inc., 2000.

"Endeavor PMA P060033 Summary of Safety and Effectiveness Data," Medtronic Vascular, 2007.

McAuliffe, et al., "Immediate and Midterm Results following Treatment of Recently Ruptured Intracranial Aneurysms with the Pipeline Embolization Device," Am J Neurordiol, 2012, vol. 33, pp. 487-493.

Dumitiriu, "Table 25.6 Medical Devices with MPC Polymer," Polymeric Biomaterials: Structures and Function, CRC Press, Dec. 2011.

Troughton, et al., "Monolayer Films Prepared by the Spontaneous Self-Assembly of Symmetrical and Unsymmetrical Dialkyl Sulfides from Solution onto Gold Substrates: Structure, Properties, and Reactivity of Constituent Functional Groups," Langmuir, 1988, vol. 4, pp. 365-385.

Fu, et al., "Surface Modification of Small Platinum Nanoclusters with Alkylamine and Alkylthiol: An XPS Study on the Influence of Organic Ligands on the Pt 4f Binding Energies of Small Platinum Nanoclusters," Journal of Colloid and Interface Science, Nov. 2001, vol. 243, Issue 2, pp. 326-330.

Product description for Lipidure-CM (MPC polymer) retrieved from http://nofamerica.net/store/index.php?dispatch=categories.view&category_id=146.

Product description for Lipidure-PC (MPC monomer) retrieved from http://nofamerica.net/store/index.php?dispatch=categories.view&category_id=145.

Product description for Reactive MPC Polymers retrieved from http://nofamerica.net/store/index.php?dispatch=categories.view&category_id=212.

* cited by examiner

|  | | Total Kill (Y / N) | | |
|---|---|---|---|---|
|  | Section / Catheter | *Pseudomonas aeruginosa* (gram negative) | *Enterococcus faecalis* (gram positive) | *Candida albicans* (yeast) |
| Sample 1, Trial 1<br><br>18 samples Total Kill<br>Broad spectrum efficacy | Top / #1 | Y | Y | Y |
| | Middle / #1 | Y | Y | Y |
| | Bottom / #1 | Y | Y | Y |
| | Top / #2 | Y | Y | Y |
| | Middle / #2 | Y | Y | Y |
| | Bottom / #2 | Y | Y | Y |
| Sample 1, Trial 2<br><br>16 samples Total Kill<br>Broad spectrum efficacy | Top / #1 | Y | trace growth | Y |
| | Middle / #1 | trace growth | Y | Y |
| | Bottom / #1 | Y | Y | Y |
| | Top / #2 | Y | Y | Y |
| | Middle / #2 | Y | Y | Y |
| | Bottom / #2 | Y | Y | Y |
| Commercial Catheter<br><br>9 samples Total Kill | Top / #1 | Y | *No* | *No* |
| | Middle / #1 | *No* | Y | Y |
| | Bottom / #1 | *No* | *No* | *No* |
| | Top / #2 | Y | Y | *No* |
| | Middle / #2 | *No* | Y | Y |
| | Bottom / #2 | *No* | Y | Y |

FIG. 3

ANTIMICROBIAL COATINGS FOR MEDICAL DEVICES AND PROCESSES FOR PREPARING SUCH COATINGS

TECHNICAL FIELD

The present disclosure relates to antimicrobial formulations and coatings for medical devices and in particular implantable medical devices and processes for preparing such formulations and coatings.

BACKGROUND

Implantable medical devices used for patient treatment can be a source of microbial infection in such patients. For example, insertion or implantation of a medical device into a patient can introduce microbes that can cause infection. To reduce or minimize the impact of the introduction of microbes to a patient, many medical devices, such as catheters, have been coated with antimicrobial agents.

However, many antimicrobial agents that are useful in coating medical devices tend to be insoluble in formulations used to coat the device and tend to form agglomerated particles on the surface of the medical device. These agglomerated particles increase the surface roughness of the medical device, thus increasing the chance for thrombus formation on the surface of the medical device, and are more readily detached from the surface thereby reducing the long term efficacy of the antimicrobial coating. Further, agglomerated particles in the antimicrobial formulation that is used to coat the medical device may lead to active material precipitating out of the formulation and therefore not being coated onto the medical device, or otherwise interfering with the coating process. Accordingly, a need exists for improved antimicrobial coatings on implantable medical devices.

SUMMARY OF THE DISCLOSURE

An advantage of the present invention is an implantable medical device having an antimicrobial coating including a water permeable polymer and uniformly dispersed particles therein of at least one antimicrobial agent. The present disclosure provides an antimicrobial formulation with little to no agglomerated particles, which can be stored over a long period of time before coating a medical device. Also, once coated onto a medical device, the coating provides a consistent elution of antimicrobial agents over a longer period of time.

These and other advantages are satisfied, at least in part, by a process of forming an antimicrobial formulation for coating a medical device. The process comprises milling at least one water permeable polymer with at least one antimicrobial agent in a liquid medium to form the antimicrobial formulation. Advantageously, the milling causes the water permeable polymer to encapsulate at least a portion of the antimicrobial agent.

An aspect of the present disclosure includes an antimicrobial formulation for coating a medical device. The formulation includes at least one water permeable polymer and particles of at least one antimicrobial agent in a liquid medium, wherein the formulation includes uniformly dispersed particles in the liquid medium with no agglomerated particles greater than 50 microns in size. The formulation can be prepared by milling the formulation.

Embodiments include any one or more of the following features, individually or combined. For example, the at least one polymer can include at least one of a polyurethane, thermoplastic polyurethane elastomer, polyester, polylactic acid, polyglycolic acid, polytetramethylene glycol, polyacrylamide, polyacrylic acid, polyacrylate, poly(2-hydroxyethyl methacrylate), polyethylene-imine, poly-sulfonate and copolymers thereof. In some embodiments, the at least one polymer has a weight average molecular weight of from about 70,000 to about 120,000 Daltons. In various embodiments, the at least one antimicrobial agent includes a combination of a silver-based antimicrobial agent and a polybiguanide or salt thereof. In still further embodiments, the silver-based antimicrobial agent includes one or more of silver particles, a silver nitrate, silver halide, silver acid salt, silver permanganate, silver sulfate, silver nitrite, silver chromate, silver carbonate, silver phosphate, silver (I) oxide, silver sulfide, silver azide, silver sulfite, a silver thiocyanate or a silver sulfonamide. In various embodiments, the polybiguanide or salt thereof includes one or more of chlorhexidine dihydrochloride, chlorhexidine diacetate or chlorhexidine digluconate. In some embodiments, the at least one antimicrobial agent includes a combination of silver sulfadiazine and chlorhexidine diacetate. In various embodiments, the liquid medium includes one or more of an alcohol; an ether; a ketone; an organic acid; an organic ester; an amide; a hydrocarbon; or a halogenated solvent or liquid. In still further embodiments, the liquid medium includes an ether and a primary $C_{1-6}$ alcohol. In various embodiments, the at least one antimicrobial agent is insoluble in the formulation and the formulation is milled until the insoluble antimicrobial agent has a mean particle size of no greater than about 50 microns. In some embodiments, the formulation includes from about 70 wt % to 90 wt % of a polyurethane polymer, from 2 wt % to about 10 wt % silver sulfadiazine, and at least 9 wt % of chlorhexidine diacetate.

In an aspect of the present disclosure, the process can comprise initially preparing a polymer solution having a viscosity in a range of from about 100 centipoise (cP) to about 1000 cP, for example, by dissolving the polymer in the liquid medium and then adding the antimicrobial agent to the solution followed by milling the formulation. The process can further comprise adding a second antimicrobial agent to the formulation after milling, and further milling the formulation with the second antimicrobial agent and further comprise adding a primary $C_{1-6}$ alcohol to the formulation after milling the formulation with the second antimicrobial agent.

In another aspect of the present disclosure, the process of forming an antimicrobial formulation for coating a medical device can comprise milling at least one water permeable thermoplastic polyurethane elastomer with a silver-based antimicrobial agent and a polybiguanide or salt thereof antimicrobial agent in a liquid medium to form the antimicrobial formulation. The process can further comprise: preparing a solution having a viscosity of from about 100 centipoise (cP) to about 1000 cP by dissolving the thermoplastic polyurethane elastomer in the liquid medium; adding the silver-based antimicrobial agent to the solution followed by milling to form a formulation; adding the polybiguanide or salt thereof antimicrobial agent to the formulation followed by milling to form the antimicrobial formulation; and adding a primary $C_{1-6}$ alcohol to the antimicrobial formulation. Advantageously, the milling can result in a formulation with significantly uniformly dispersed particles and with no, or very few, agglomerated particles greater than 50 microns.

Another aspect of the present disclosure includes a process of forming an antimicrobial coating on a medical device. The process comprises applying an antimicrobial formulation having at least one water permeable polymer and at least one antimicrobial agent on a medical device to form an antimicrobial coating on the medical device, wherein the antimicrobial formulation is formed by milling the at least one polymer with the at least one antimicrobial agent in a liquid medium.

Embodiments include any one or more of the features described for the process of forming the antimicrobial formulation and/or formulation and/or any one or more of the following features, individually or combined. In addition, the medical device can be selected from the group consisting of a dialysis catheter, a urological catheter, an enteral feeding tube, a surgical staple, a trocar, an implant, suture, a respiratory tube, a surgical plate, a surgical screw, a wire, and a hernia mesh. In some embodiments, the coating has a thickness in a range of between about 20 microns to about 80 microns. In various embodiments, applying the formulation on the medical device comprises dip-coating the medical device in the formulation and then drying the antimicrobial formulation by driving off the liquid medium to form the antimicrobial coating on the medical device. In embodiments, the at least one polymer includes a polyurethane polymer and the at least one antimicrobial agent includes a combination of a silver-based antimicrobial agent and a polybiguanide or salt thereof. In various embodiments, the at least one antimicrobial agent includes a combination of silver sulfadiazine and chlorhexidine diacetate.

Another aspect of the present disclosure includes a device having an antimicrobial coating, wherein the coating comprises a polymer and uniformly dispersed particles of at least one antimicrobial agent and wherein the particles and any agglomerations of the antimicrobial agent have an average size of no greater than 50 microns.

Embodiments include any one or more of the features described for the antimicrobial formulation and/or the process of forming the antimicrobial formulation and/or the process of forming the coating on the medical device and/or any one or more of the following features, individually or combined. In addition, the at least one antimicrobial agent can be a silver-based antimicrobial agent. In some embodiments, the at least one antimicrobial agent is a silver sulfadiazine. In various embodiments, the at least one antimicrobial agent is a silver sulfadiazine and wherein the coating has a release profile wherein at least 0.50 µg/cm of silver is continuously released after 72 hours. In still further embodiments, the coating further comprises chlorhexidine diacetate and/or the coating further comprises chlorhexidine diacetate and at least 10 µg/cm of chlorhexidine diacetate is continuously released after 72 hours. In various embodiments, the antimicrobial coating is formed on the device by applying an antimicrobial formulation having at least one water permeable polymer and at least one antimicrobial agent on the medical device. In embodiments, the antimicrobial formulation is formed by milling the at least one polymer with the at least one antimicrobial agent in a liquid medium. In some embodiments, the antimicrobial coating includes from about 70 wt % to 90 wt % of a polyurethane polymer, from 2 wt % to about 10 wt % silver sulfadiazine, and at least 9 wt % of chlorhexidine diacetate.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 3 is a chart showing the results of bacterial challenge testing (BAC) for catheter samples having an antimicrobial coating in accordance with the present disclosure compared to two catheter samples of a commercially available catheter having an antimicrobial coating.

FIG. 4A shows an SEM image of an antimicrobial coating that was prepared from an antimicrobial formulation which was prepared by milling the components of the formulation and FIG. 4B shows an SEM image of an antimicrobial coating from the same formulation which was prepared by mixing, not milling the components.

FIG. 5A shows an SEM image of an antimicrobial coating prepared in accordance with the present disclosure. FIG. 5B shows an SEM image of a commercially available catheter having an antimicrobial coating.

FIG. 6A shows an SEM image of an antimicrobial coating prepared in accordance with the present disclosure. FIG. 6B shows an SEM image of a commercially available catheter having an antimicrobial coating.

DETAILED DESCRIPTION OF THE DISCLOSURE

Figure 1:
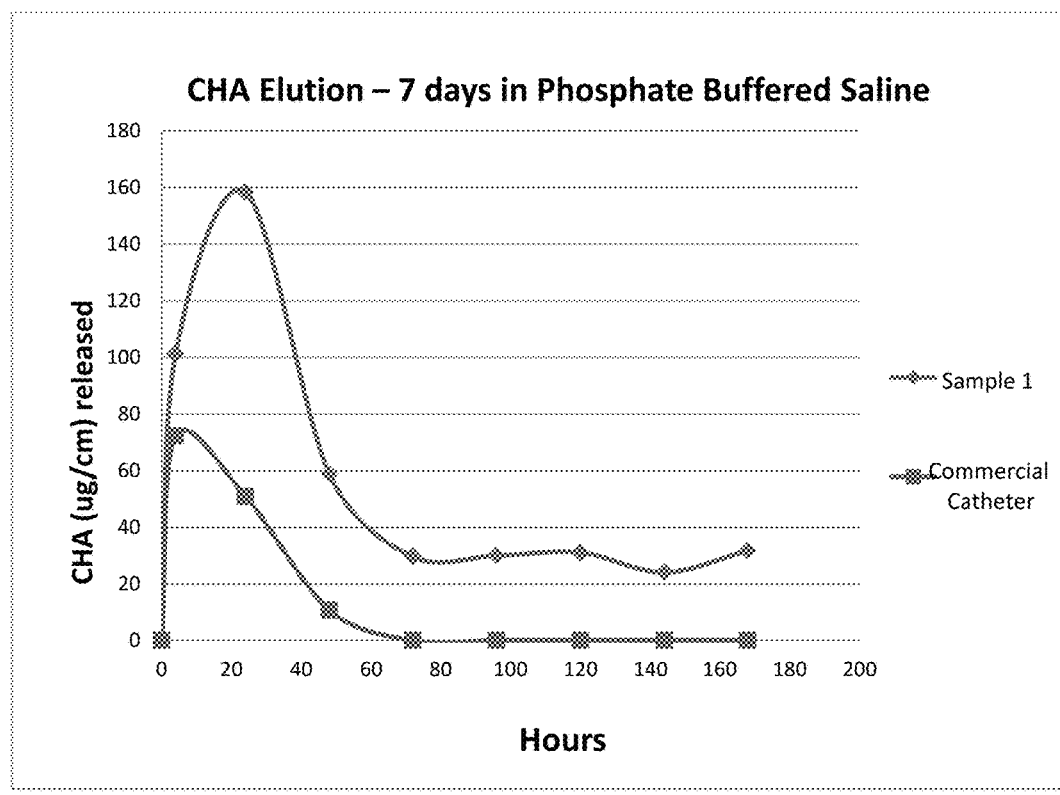
FIG. 1 is a chart showing the release profile of a catheter coated with chlorhexidine acetate (CHA) prepared in accordance with the present disclosure compared to a commercial catheter having an antimicrobial coating including CHA.

The present disclosure is directed to antimicrobial formulations that can be applied to medical devices to form antimicrobial coatings thereon. The present disclosure is particularly applicable to implantable medical devices, such as catheters, enteral feeding tubes, surgical staples, respiratory tubes, surgical plates, surgical screws, wires, and hernia mesh, and forming antimicrobial coatings thereon.

Since many polymers and/or antimicrobial agents that are useful for forming antimicrobial coatings on medical devices are not readily soluble, such ingredients tend to form agglomerated particles in the formulations used to coat a medical device as well as on the surface of the medical device. Agglomerated particles can form in sizes as large as several hundred microns even when the initial size of the particles used in preparing a formulation is as small as several microns. These agglomerated particles are due to the agglomeration of many smaller sized particles that agglomerate during the coating process.

These agglomerated particles adversely increase the surface roughness of the medical device. In addition, the size and shape of the agglomerated particles can adversely affect the dissolution or release of the antimicrobial agent from the coating.

Antimicrobial formulations of the present disclosure are prepared by milling the various ingredients, thereby minimizing the size of the insoluble particles and their tendency to agglomerate. Surprisingly, it has been found that by milling the various components as set forth below, not only is the coating prepared from the formulation more smooth once coated on a medical device, but also the elution rate of the antimicrobial agents becomes more consistent over time, and the release rate appears to be better controlled over a longer period of time. Further, re-agglomeration of the insoluble antimicrobial components is eliminated, or nearly eliminated.

In practicing embodiments of the present disclosure, an antimicrobial formulation for coating a medical device can be formed by milling at least one polymer with at least one antimicrobial agent in a liquid medium to form the antimicrobial formulation. Preferably, the milling is done by a high-shear miller that reduces particle size and prevents agglomeration of particles in the formulation. Formulations containing one or more insoluble ingredients are particularly useful in practicing the present disclosure. Such formulations contain a liquid medium, at least one polymer, and at least one antimicrobial agent that is not soluble in the formulation. The formulation can also include other ingredients that are useful in forming antimicrobial coatings on implantable medical devices.

Polymers useful for practicing the present disclosure include those that are water permeable and are used for coating medical devices such as, for example, a polyurethane, such as a thermoplastic polyurethane elastomer, a polyester, polylactic acid, polyglycolic acid, polytetramethylene glycol, polyacrylamide, polyacrylic acid, polyacrylate, poly(2-hydroxyethyl methacrylate), polyethylene-imine, poly-sulfonate and copolymers thereof such as poly(lactic acid-co-glycolic acid) (PLA/PGA), polyacrylic-co-hydroxylated-acrylate, poly(acrylic acid-co-2-hydroxy ethyl methacrylate). In one aspect of the present disclosure, the polymer is a thermoplastic polyurethane elastomer, such as Pellethane which is available from Lubrizol Advanced Materials, USA.

The molecular weight of the polymer is preferably high enough to form a useful coating on the medical device but not so high as to prevent the formulation from flowing over the medical device and forming the coating. Such polymers have a weight average molecular weight, for example, of from about 20,000 to about 500,000 Daltons, e.g. between about 50,000 to about 200,000, between about 70,000 to about 120,000 Daltons. The weight average molecular weights can be determined by using GPC analysis having a refractive index detector coupled with a light scattering detector for absolute molecular weight measurement of weight average molecular weight ($M_w$).

Antimicrobial agents that are useful for the present disclosure include, for example, silver-based antimicrobial agents; polybiguanides and salts thereof; chlorhexidine and salts thereof such as the dihydrochloride, diacetate and digluconate salt of chlorhexidine; hexachlorophene; cyclohexidine; chloroaromatic compounds such as triclosan; para-chloro-meta-xylenol.

Silver-based antimicrobial agents include, for example, silver particles; a silver nitrate; silver halides, e.g., silver fluoride, chloride, bromate, iodate; silver acid salts, e.g., silver acetate, silver salicylate, silver citrate, silver stearate, silver benzoate, silver oxalate; silver permanganate; silver sulfate; a silver nitrite; silver dichromate; silver chromate; silver carbonate; silver phosphate; silver (I) oxide; silver sulfide; silver azide; silver sulfite; silver thiocyanate; and silver sulfonamide, such as a silver sulfadiazine. Antimicrobial agents that are not readily soluble in a formulation are particularly advantageous in the present disclosure.

In one embodiment of the present disclosure, the antimicrobial agents include a combination of a silver-based salt and a polybiguanide salt, i.e., a combination of silver sulfadiazine and chlorhexidine diacetate.

The liquid medium of the present disclosure includes one or more liquids that are useful for coating a medical device and dissolving or suspending the polymer and/or antimicrobial agent. Such liquids include, for example, one or more of the following: an alcohol and lower alcohol, e.g., a $C_{1-12}$ alcohol, such as methanol, ethanol, n-propanol, isopropanol, n-butanol, isobutanol, furfuryl alcohol; a polyhydridic alcohol, such as ethylene glycol, a butanediol, a propanediol; an ether, such as a linear, branched or cyclic lower ether, dimethyl ether, ethyl ether, methyl ethyl ether, tetrahydrofuran; a ketone such as a linear, branched or cyclic lower ketone, such as acetone, methyl ethyl ketone, cyclohexanone; an organic acid, such as formic acid, acetic acid, butyric acid, benzoic acid; an organic ester, such as a formate, ethyl or methyl acetate, propionate; an amide such as a linear, branched or cyclic lower amide, such as dimethylacetamide (DMAC), pyrrolidone, 1-Methyl-2-pyrrolidinone (NMP), a hydrocarbon, such as a linear, branched or cyclic alkane, such as a pentane, hexane, heptane, octane, cyclohexane, a linear, branched or cyclic alkene, an aromatic solvent or liquid; and a halogenated solvent or liquid such as a chlorinated solvent or liquid.

In one aspect of the present disclosure, the liquid medium includes a primary alcohol, e.g., a primary $C_{1-6}$ alcohol such as methanol, ethanol, n-propanol, n-butanol, n-pentanol, n-hexanol in the formulation. It was found that use of a primary $C_{1-6}$ alcohol, such as n-propanol, facilitates coating of the medical device. It was found that n-propanol has a beneficial balance between the length of the aliphatic chain and the hydroxyl group. Also, when used with THF, n-propanol has a desirable boiling point of 99° C., which allows it to stay at the coating surface longer than THF which in turn improves flow and leveling of the coating on the medical device surface.

Milling the one or more polymers and antimicrobial agents in liquid media offers the advantage of forming uniform antimicrobial formulations that can be used to coat medical devices. It is believed that milling, rather than mixing such as with a high shear mixer, a liquid medium including the at least one water permeable polymer with the at least one antimicrobial agent enables the antimicrobial agent to be uniformly dispersed in the liquid medium and/or to be encapsulated within the polymer such that the antimicrobial agent does not re-agglomerate prior to and during coating of a medical device. The encapsulated agent in the formulation is believed to provide a more consistent elution rate and prevent the re-agglomeration of particles over time. Milling the formulation can be carried out using a high-shear miller such as a roll mill. Milling media useful for the present disclosure include Yttria stabilized zirconia grinding media, ⅜ inch cylinder shape, from Inframat Advanced Materials.

In one aspect of the present disclosure, at least one antimicrobial agent is insoluble in the formulation and the formulation is milled until the insoluble antimicrobial agent has a mean particle size of no greater than about 50 microns, such as no greater than 40 microns, 30 microns, 20 microns, 10 microns, 5 microns and numbers therebetween. In one embodiment, the mean particle size is approximately 5 microns. Mean particle size determinations can be made by a laser diffraction particle size analyzer, such as the Microtrac S3500 with a circulating loop to suspend the sample during analysis.

In an embodiment of the present disclosure, the milling process can include initially preparing a polymer solution. Such polymer solutions preferably have a viscosity and wetting properties that allows the formulation to smoothly flow over the surface of the device to facilitate forming a uniform coating on the medical device. The amount of the polymer in the formulation to provide an appropriate viscosity will depend on the polymer, liquid medium and molecular weight of the polymer.

Viscosities suitable for the formulation range from about 100 centipoise (cP) to about 10,000 cP, e.g. from about 100 cP to about 1,000 cP, preferably from about 500 cP to about 1000 cP. Typically from about 5 wt % to 30 wt % of the polymer can be combined with the liquid medium to form the solution with the appropriate viscosity. In an embodiment of the present disclosure, preparing an antimicrobial formulation includes initially preparing a polymer solution having a viscosity of from about 100 centipoise (cP) to about 1,000 cP by dissolving the polymer in the liquid medium and then adding the antimicrobial agent to the solution followed by milling the formulation.

Additional antimicrobial agents can be added to such a formulation. Such additional antimicrobial agents can be added neat or in a solution with a liquid medium such as in a primary $C_{1-6}$ alcohol. After adding additional antimicrobial agents, the formulation can be milled to form a more or less homogeneous mixture with particles having a mean particle size of no greater than about 50 microns, such as no greater than 40 microns, 30 microns, 20 microns, 10 microns, 5 microns and numbers there between.

Medical devices can be prepared having antimicrobial coatings from the formulations of the present disclosure. In practicing certain embodiments of the present disclosure, an antimicrobial coating on a medical device can be prepared by applying an antimicrobial formulation having at least one polymer and at least one antimicrobial agent on a medical device. The application of the formulation to the device can be by a dip-coating process or by a spraying process, for example. As described above, a formulation including at least one insoluble ingredient is particularly advantageous in practicing the present disclosure. The formulation is formed by milling the at least one polymer with the at least one antimicrobial agent in a liquid medium.

Medical devices that can be coated by the processes described in the present disclosure include, for example, any medical device intended to be implanted in a patient such as dialysis catheters, urological catheters, enteral feeding tubes, staples, trocars, implants, titanium implants, respiratory tubes, surgical plates, surgical screws, wires, hernia mesh, and sutures.

This formulation can be applied to the medical device in any way that allows the formulation to flow over and coat the device. For example, the formulation can be applied by a dip-coating process wherein the medical device is dipped into a container holding the formulation and then removed from the container. The formulation is then allowed to dry on the device. Drying can include heating the coated medical device or allowing the medical device to dry at room temperature. In an embodiment of the present invention, the formulation includes a polyurethane polymer and an antimicrobial agent that includes a combination of a silver based antimicrobial agent and a polybiguanide or salt thereof, i.e., a combination of silver sulfadiazine and chlorhexidine diacetate.

The thickness of the antimicrobial coating on the medical device will depend on the application of the medical device. For example, when coating a dialysis catheter the coating can have a thickness of between about 20 microns to about 80 microns (e.g., between about 65 to about 45 microns such as about 55 microns). Different implantable medical devices can have the same thickness of coatings depending on the intended use.

In practicing embodiments of the present disclosure, a medical device can be prepared having an antimicrobial coating which includes a polymer and particles of at least one antimicrobial agent wherein the particles of the antimicrobial agent have an average size of no greater than the average particle size of the antimicrobial agent in the initial formulation. That is, the mean particle size of the antimicrobial agent on or in the coating is no greater than about 50 microns, 40 microns, 30 microns, 20 microns, 10 microns, 5 microns and numbers therebetween.

Advantageously, the particles formed in the formulation after milling resist agglomeration both in the bulk formulation and when prepared as a coating on the medical device. The coating can contain particles having a mean particle size and mean agglomeration size of no greater than about 50 microns, 40 microns, 30 microns, 20 microns, 10 microns, 5 microns, and numbers therebetween.

The solubility of the antimicrobial agents and the water permeability of the polymer will affect the release rate of the antimicrobial agent from the coating. For example more soluble antimicrobial agents such as chlorhexidine gluconate will have a high release rate whereas the relatively water insoluble hydrochloride salt releases slowly. In one embodiment of the present disclosure, the coating on the medical device has a nominal formulation that includes from about 70 wt % to 90 wt % of a polyurethane polymer, from 2 wt % to about 10 wt % silver sulfadiazine, e.g. from about 3.5 wt % to about 7 wt % and a minimum amount of CHA of about 9 wt %, 10 wt %, or about 11 wt %. Such a coating can be formed to have a release profile wherein at least 0.50 µg/cm of silver is continuously released after 75 hours, e.g., after about 100 hours, 150 hours and higher, and wherein at least 10 µg/cm of chlorhexidine diacetate is continuously released after 75 hours e.g., after about 100 hours, 150 hours and higher.

Examples

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

A series of antimicrobial formulations were prepared by initially preparing an approximate 12 wt % polymer solution. This was accomplished by combining a thermoplastic polyurethane elastomer polymer (Pellethane 2363-80A thermoplastic polyurethane polymer available from Lubrizol) with Tetrahydrofuran (THF) in a polymer reactor. Four different thermoplastic polyurethane elastomer polymers were used which had weight average molecular weights of about 82,400, 89,700, 90,400, and 105,900 Daltons, which were determined by GPC equipped with a refractive index detector coupled with a light scattering detector for absolute molecular weight measurement ($M_w$). These polymer solutions had Brookfield viscosity values of 1167, 1686, 1533, and 3965 cP, respectively as determined from a Brookfield viscometer in THF with approximately 12.5 wt % solids. The polymer reactor was configured with a reflux condenser, stirring mechanism and Nitrogen gas inlet to provide a constant Nitrogen blanket in the reactor. THF was added to the reactor and the polyurethane polymer was added to a level of 12.3 weight percent solids, and the mixture was heated with mixing at 45-55° C. for 16 hours, then cooled to ambient temperature to form the solution containing the polymer. The percent solids of the polyurethane polymer solution was measured gravimetrically, by placing a sample on an aluminum weighing dish in a lab oven at 110° C. for 60 minutes.

A mixture containing the polymer solution utilizing the polyurethane having a molecular weight of 89,700 Daltons and a silver-based antimicrobial agent was then prepared by combining 181.22 grams of the polyurethane polymer/THF solution with 91.78 grams of THF and with 2.81 grams of silver sulfadiazine (AgSD) in a one (1) quart sealed glass jar milling vessel together with milling media, i.e., zirconia grinding media. This mixture was then milled for 24 hours in the sealed glass jar milling vessel on a roll mill using 555 grams (114 media pieces) of Yttria stabilized Zirconia grinding media ⅜ inch cylinder shape (available from Inframat Advanced Materials). The milling rate was set to about 50 rpm for this and subsequent milling.

A mixture of chlorhexidine acetate (CHA) (available from Medichem, S.A., Barcelona Spain) was separately prepared by combining 4.64 grams of CHA with 9.30 grams of methanol with mixing until complete dissolution was achieved. Then 12.4 grams of THF was slowly added to the CHA/methanol solution with mixing.

The CHA/methanol/THF solution was then added to the milling vessel containing the polyurethane/THF/AgSD mixture, with mixing, in increments of equal volume at approximately every 1 hour interval for a total 6 hour time period. This mixture was then milled for 24 hours.

Additional processing aids and solvents can be added to the milled mixture. For this example, approximately 98.6 grams of n-propanol was added in increments of equal volume over 2 hours while milling, and the mixture was milled for an additional 3 hours to provide an antimicrobial formulation. Milling was conducted throughout the n-propanol addition. N-propanol was added in 2 increments of equal volume, then milled for an additional 3 hours. For this example, n-propanol was the let-back solvent used to dilute the formulation to reduce the overall amount of the THF, and to provide improved flow/leveling of the coating on drying. This formulation had the following weight percentages:

TABLE 1

Example Antimicrobial Formulation

| Ingredient | Approximate Weight % |
|---|---|
| Polyurethane polymer | 8.41 |
| AgSD | 0.70 |
| CHA | 1.16 |
| THF | 62.81 |
| Methanol | 2.32 |
| n-propanol | 24.60 |
| Total | 100 |

The percent solids of the formulation was measured gravimetrically, by placing a sample on an aluminum weighing dish in a lab oven at 110° C. for 60 minutes. The viscosity of the formulation was measured using a Brookfield viscometer.

Figure 7:
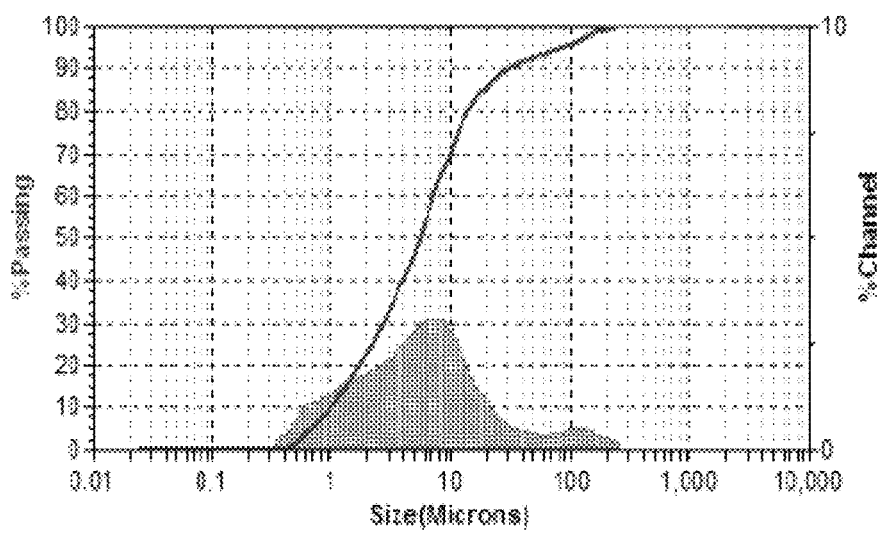
FIG. 7 is a particle size distribution chart of an antimicrobial formulation prepared in accordance with the present disclosure.

The particle sizes for AgSD after milling is shown in FIG. 7. The particle sizes for AgSD after milling had a distribution wherein the 50 percentile value was approximately 5.4 microns and 90% of the particles were 30 microns or less. The mean particle size was 5.4 microns. The foregoing particle sizes were determined by a laser diffraction particle size analyzer, the Microtrac S3500 with a circulating loop to suspend the sample during analysis. Specifically, the formulation was stirred on a lab stir plate with a stir bar at 600 rpm for 2 hours. The formulation was diluted with tetrahydrofuran (THF) solvent to adjust the viscosity into the appropriate range for the instrument, and automatic mixing of the sample was maintained throughout the particle size measurements to generate the particle size distribution chart shown in FIG. 7. While the particle size distribution shows few particles over 100 microns, it is believed, based on SEM images of the coating, that few particles are actually over 50 microns, and that the population at the high end of the distribution chart may actually be the laser detecting multiple particles in close proximity to each other while the diluted sample was mixing during analysis.

The antimicrobial formulation was used to prepare an antimicrobial coating on the exterior of the dialysis catheter surface. This was accomplished by placing the formulation in a suitable vessel inside an automated dip-coating apparatus (appropriately vented) and submerging the catheter shaft into the formulation. The catheter was then dried in a vented oven at 60° C. for 5 days to remove the solvents. The coating prepared in this example was composed approximately of 81.88 wt % polyurethane polymer, 11.30 wt % CHA and 6.82% AgSD. The thickness of the coating was measured by obtaining a cross-section of the catheter at various intervals and obtaining the coating thickness by measurement on a Scanning Electron Microscope. The thickness was determined to be about 55 microns.

Catheters prepared according to this example were tested for the release rates of the antimicrobial agents in phosphate buffered saline (PBS) solution. The release rates were determined by taking samples of PBS solution from a container holding cut samples of the coatings of each catheter. For each catheter, several samples of the coating were prepared by cutting the coated catheter to a particular size. The cut samples were then combined with PBS solution in a sample container mounted on a shaker which was set to 37° C. and 120 rpm. The cut coating samples were then removed from the container and placed in new sample containers with PBS solutions first at the 4 hour mark, then at every 24 hours thereafter. The PBS solutions were then analyzed for antimicrobial content. Chlorhexidine was analyzed by HPLC and silver concentration was analyzed by ICP-MS.

Figure 2:
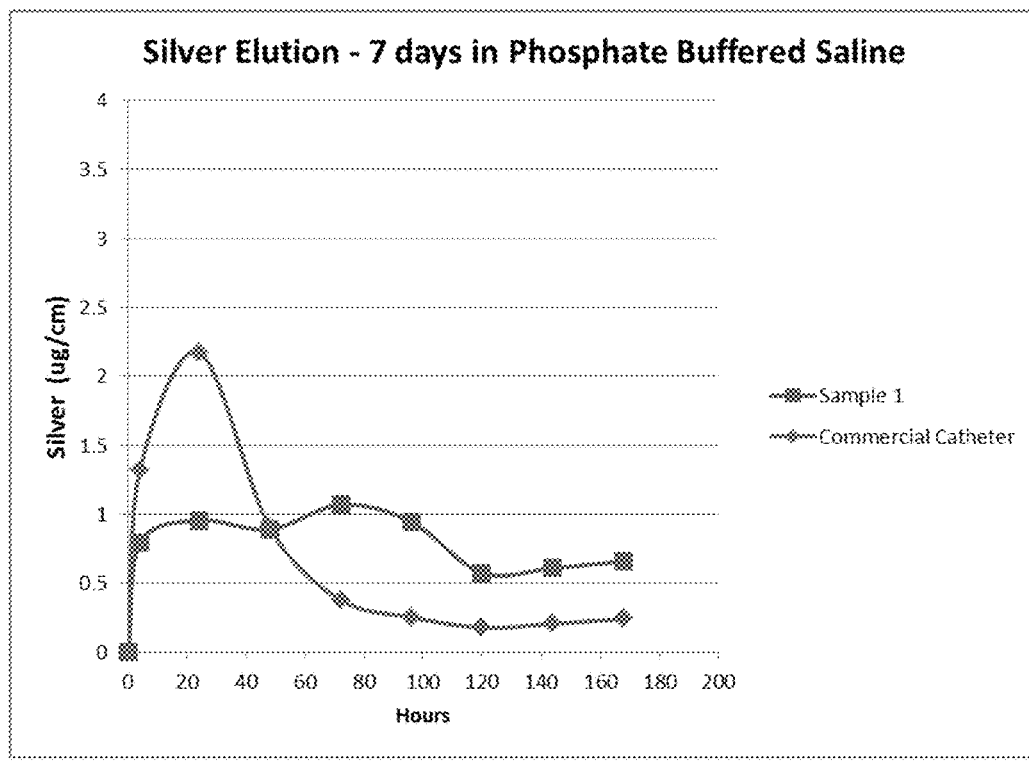
FIG. 2 is a chart showing the release profile of silver from an antimicrobial coating in accordance with the present disclosure compared to a commercially available catheter having an antimicrobial coating including silver.

Release rates for the antimicrobial agents were measured as described above and the results plotted in the charts shown in FIGS. 1 and 2. FIGS. 1 and 2 also plot the release rates of a commercially available catheter, the ARROWgard Blue™ hemodialysis catheter available from Teleflex Medical (Research Triangle Park, N.C.), having an antimicrobial coating including AgSD and CHA. The ARROWgard Blue™ catheter has been commercially available since approximately 1990, and it is believed, based on Food and Drug Administration filings, that the only change to the antimicrobial coating since its commercial release has been an increase in the antimicrobial material amounts. The ARROWgard Blue™ catheter samples were prepared and analyzed in PBS as described above. As shown in FIGS. 1 and 2, catheters coated with a formulation according to the present disclosure had at least 10 µg/cm of chlorhexidine diacetate released after 72 hours and a release profile wherein at least 0.50 µg/cm of silver was released after 72 hours. For this particular example, the 10 µg/cm of chlorhexidine diacetate released after 150 hours and had a release profile wherein at least 0.50 µg/cm of silver was released after 150 hours.

Catheters prepared according to this example were also compared to the commercially available ARROWgard Blue™ catheter for antimicrobial effectiveness. FIG. 3 shows Bacterial Challenge (BAC) Testing of the catheters. The data show that catheters coated with formulations of the present disclosure had superior antimicrobial activity across all 3 microorganisms as compared to the commercially available catheter.

Figure 4A:
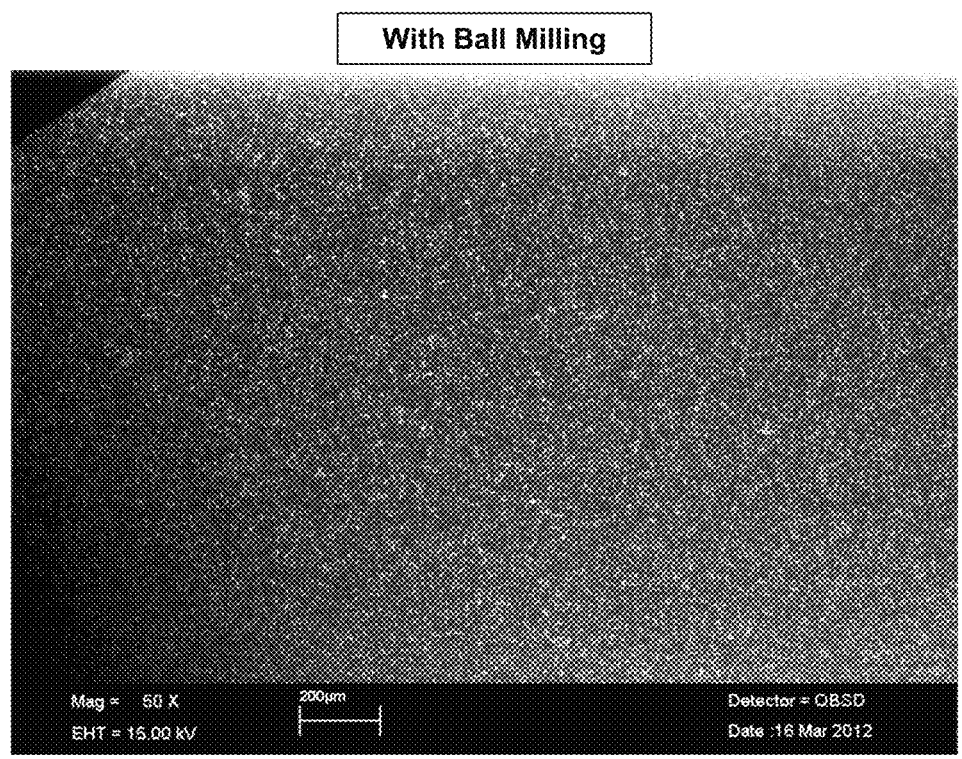
FIGS. 4A and 4B are SEM images of antimicrobial coatings on medical devices.
Figure 4B:
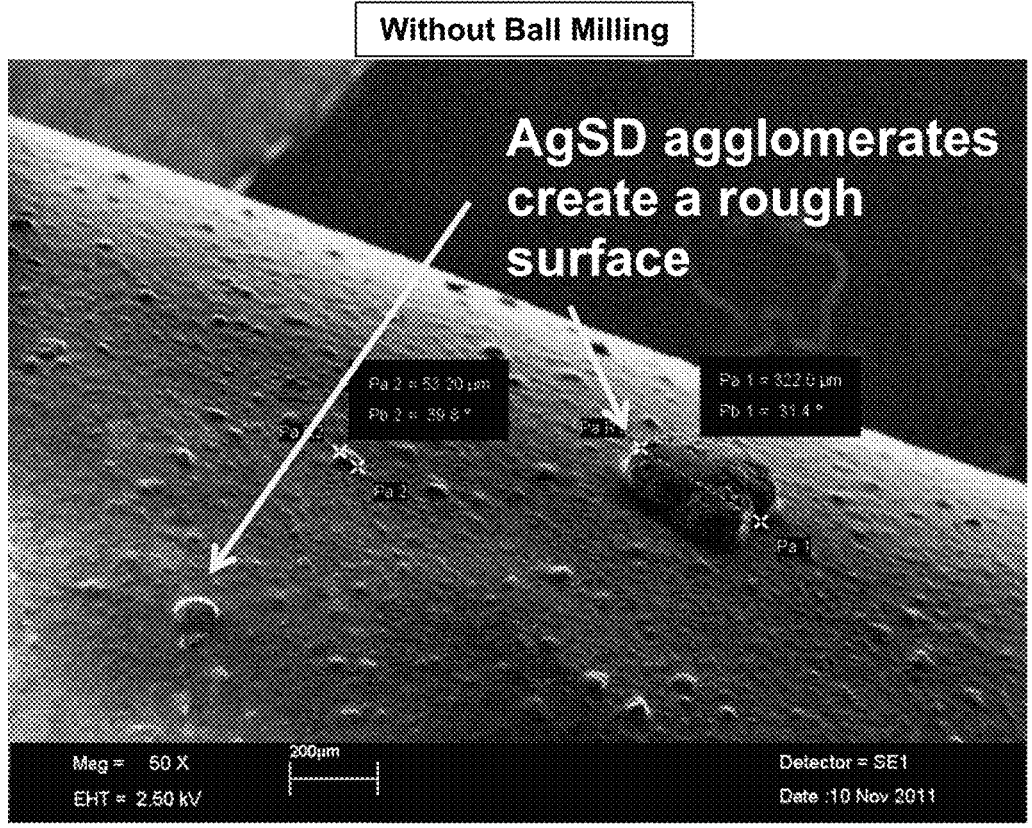

To demonstrate the benefits of milling the components of an antimicrobial formulation, a comparative example was undertaken. Two separate antimicrobial formulations were prepared with the same polymer, antimicrobial agents and liquid media. One formulation was prepared by milling the components while the other formulation was prepared by mixing the components. Coatings were then prepared from the two formulation and the coatings were analyzed by SEM. The SEM images are shown in FIGS. 4A and 4B. FIG. 4A shows an SEM image of an antimicrobial coating that was prepared from the formulation with milling and FIG. 4B shows an SEM image of the formulation prepared by mixing, not milling the components.

As shown in FIGS. 4A and 4B, the antimicrobial formulation that was prepared by a process that included milling of the components resulted in a coating with uniformly dispersed particles, with uniformly sized particles and with no agglomerated particles greater than 20 microns. As can be seen from FIG. 4B, the antimicrobial formulation prepared without milling resulted in a coating with a non-uniform distribution of particles and agglomerated particles of greater than 50 microns. In FIG. 4B, a 53 micron and 322 micron agglomerated particle were visible in the image.

Figure 5A:
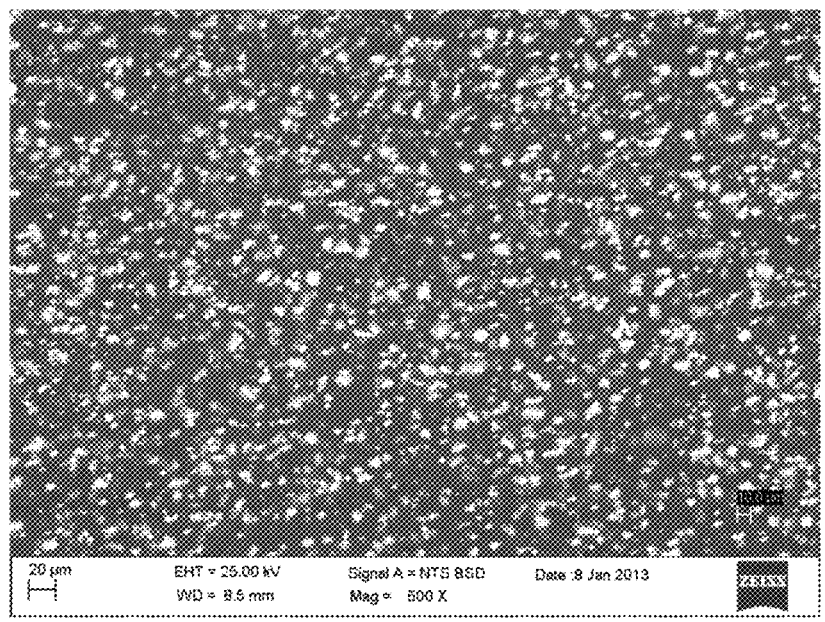
FIGS. 5A and 5B are SEM images of antimicrobial coatings on medical devices.
Figure 5B:
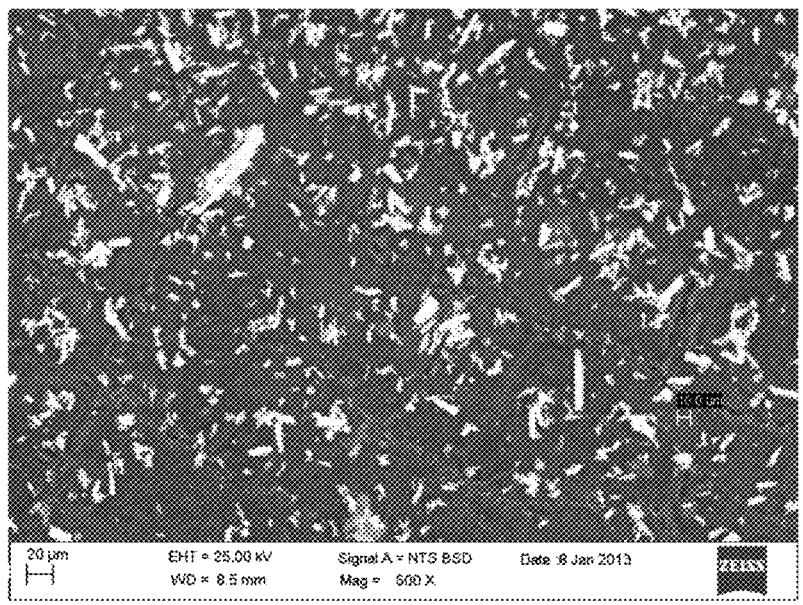

Similarly, SEM imaging was conducted of an antimicrobial coating that was prepared from the formulation of the present disclosure (shown in FIG. 5A), as well as the commercially available ARROWgard Blue™ catheter (shown in FIG. 5B). As shown in FIG. 5A, the antimicrobial formulation that was prepared by a process that included milling of the components as described above resulted in a coating with uniformly dispersed particles, with uniformly sized particles and with no agglomerated particles greater than 20 microns. As can be seen from FIG. 5B, the antimicrobial coating on the commercially available ARROWgard Blue™ catheter has a coating with a non-uniform distribution of particles and agglomerated particles of greater than 20 microns.

Figure 6A:
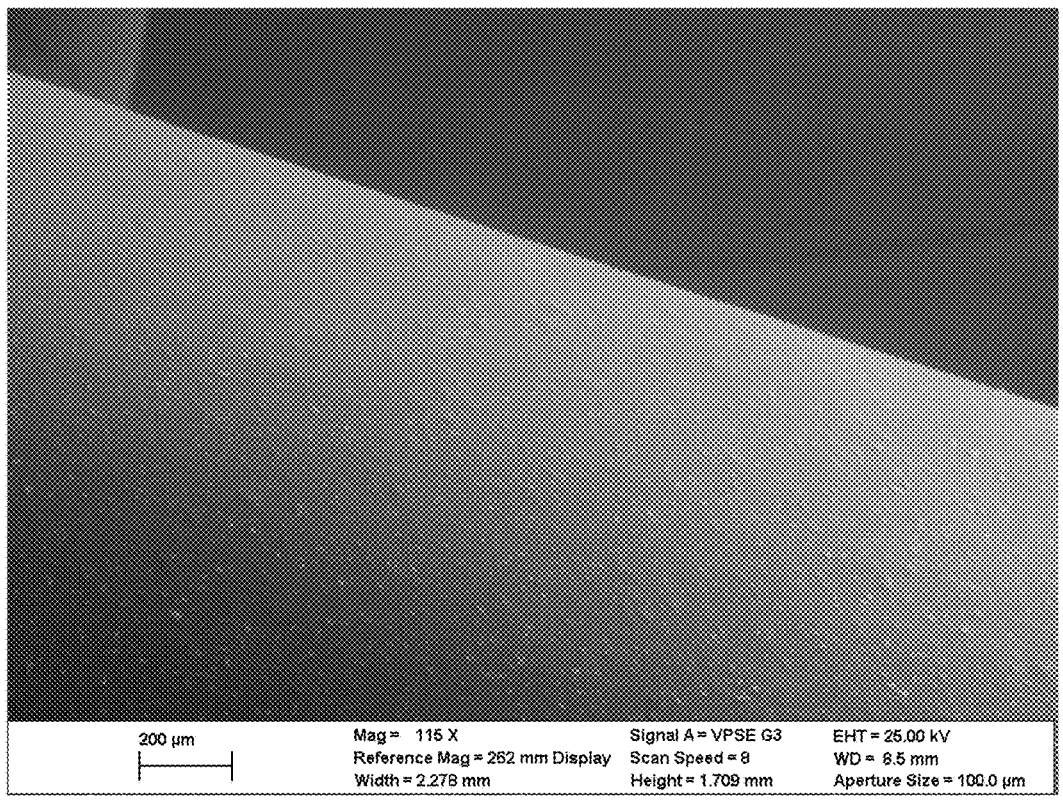
FIGS. 6A and 6B are SEM images of antimicrobial coatings on medical devices.
Figure 6B:
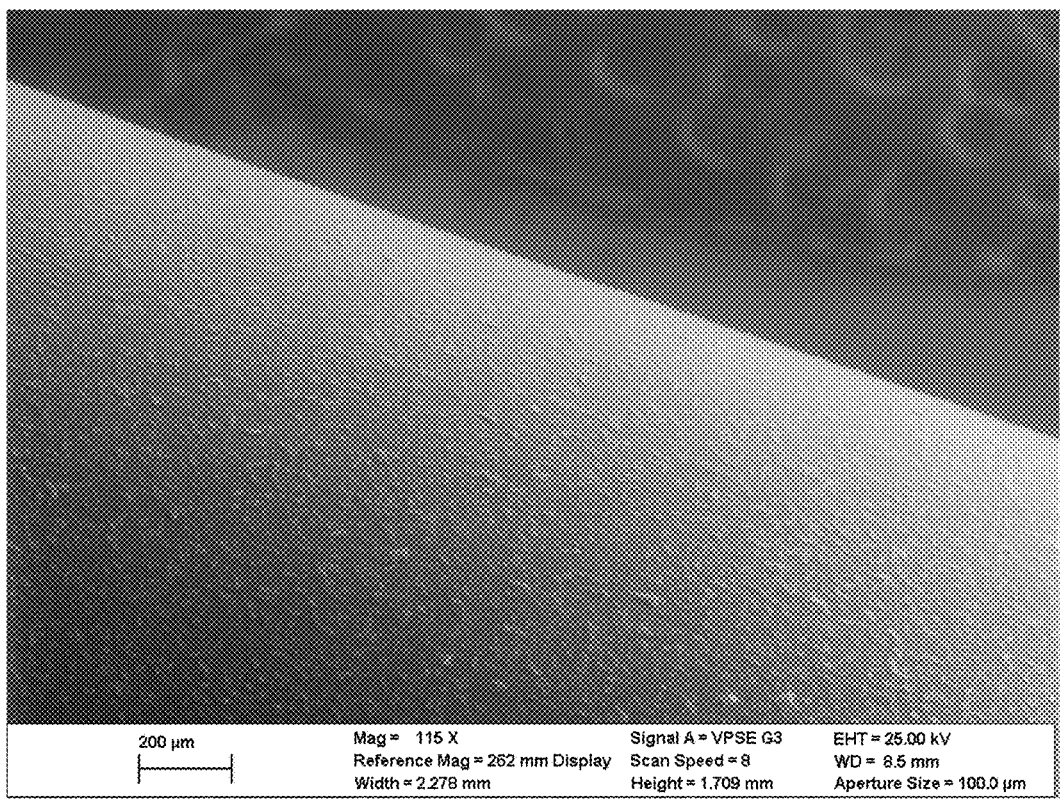

SEM imaging was conducted of an antimicrobial coating that was prepared from the formulation of the present disclosure (shown in FIG. 6A), as well as the commercially available ARROWgard Blue™ catheter (shown in FIG. 6B) to show the surface texture. As shown in FIG. 6A, the antimicrobial formulation that was prepared by a process that included milling of the components as described above resulted in a coating with a smooth outer surface. As can be seen from FIG. 6B, the antimicrobial coating on the commercially available ARROWgard Blue™ catheter has a coating with a surface texture that is less smooth in appearance than that of the coating of the present disclosure.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A process of forming an antimicrobial formulation for coating a medical device, the process comprising milling at least one water permeable polymer which is dissolved in a liquid medium with at least one antimicrobial agent which is insoluble in the liquid medium to form the antimicrobial formulation in which the at least one water permeable polymer encapsulates the at least one antimicrobial agent; and adding a primary $C_{1-6}$ alcohol to the antimicrobial formulation;
   wherein the at least one antimicrobial agent includes a silver-based antimicrobial agent and wherein the at least one water permeable polymer includes at least one of a polyurethane or a thermoplastic polyurethane elastomer.

2. The process of claim 1, wherein the at least one water permeable polymer has a weight average molecular weight of from about 70,000 to about 120,000 Daltons.

3. The process of claim 1, wherein the at least one antimicrobial agent includes the silver-based antimicrobial agent and a second antimicrobial agent which is a polybiguanide or salt thereof.

4. The process of claim 1, wherein the at least one antimicrobial agent includes silver sulfadiazine, as the silver-based antimicrobial agent, and a second antimicrobial agent which is chlorhexidine diacetate.

5. The process of claim 1, wherein the liquid medium includes one or more of an alcohol; an ether; a ketone; an organic acid; an organic ester; an amide; a hydrocarbon; or a halogenated solvent or liquid.

6. The process of claim 1, wherein the liquid medium includes an ether and a primary $C_{1-6}$ alcohol.

7. The process of claim 1, wherein the at least one antimicrobial agent is insoluble in the formulation and the formulation is milled until the insoluble antimicrobial agent has a mean particle size of no greater than 50 microns.

8. The process of claim 1, comprising initially preparing a polymer solution having a viscosity of from about 100 centipoise (cP) to about 1000 cP by dissolving the at least one water permeable polymer in the liquid medium and then adding the antimicrobial agent to the solution followed by milling the formulation.

9. The process of claim 8, further comprising adding a second antimicrobial agent to the formulation after milling, and further milling the formulation with the second antimicrobial agent.

10. The process of claim 9, wherein the primary $C_{1-6}$ alcohol is methanol, ethanol, n-propanol, n-butanol, n-pentanol, and/or n-hexanol.

11. A process of forming an antimicrobial coating on a medical device, the process comprising:
   applying the antimicrobial formulation of claim 1 on a medical device to form an antimicrobial coating on the medical device.

12. The process of claim 11, wherein the medical device is selected from the group consisting of a dialysis catheter, a urological catheter, an enteral feeding tube, a surgical staple, a trocar, an implant, suture, a respiratory tube, a surgical plate, a surgical screw, a wire, and a hernia mesh.

13. The process of claim 11, wherein the coating has a thickness of between about 20 microns to about 80 microns.

14. The process of claim 11, wherein applying the formulation on the medical device comprises dip-coating the medical device in the formulation and then drying the antimicrobial formulation by driving off the liquid medium to form the antimicrobial coating on the medical device.

15. The process of claim 11, wherein the at least one antimicrobial agent includes a combination of silver sulfadiazine and chlorhexidine diacetate.

* * * * *